(12) United States Patent
Eltorai et al.

(10) Patent No.: US 10,925,746 B2
(45) Date of Patent: Feb. 23, 2021

(54) PATIENT SPECIFIC CARPAL IMPLANT

(71) Applicant: Orthopedix, Inc., Louisville, KY (US)

(72) Inventors: Adam E. M. Eltorai, Louisville, KY (US); Ashok Seetharam, Louisville, KY (US); Vishal J. Thomas, Louisville, KY (US)

(*) Notice: Subject to any disclaimer, the term of this patent is extended or adjusted under 35 U.S.C. 154(b) by 2 days.

(21) Appl. No.: 16/045,680

(22) Filed: Jul. 25, 2018

(65) Prior Publication Data
US 2020/0030109 A1 Jan. 30, 2020

(51) Int. Cl.
*A61F 2/42* (2006.01)
*A61F 2/30* (2006.01)

(52) U.S. Cl.
CPC ........ *A61F 2/4261* (2013.01); *A61F 2/30771* (2013.01); *A61F 2/30942* (2013.01); *A61F 2002/3096* (2013.01); *A61F 2002/30621* (2013.01); *A61F 2002/30772* (2013.01); *A61F 2002/4271* (2013.01); *A61F 2310/00023* (2013.01)

(58) Field of Classification Search
CPC ................ A61F 2/42; A61F 2002/4256; A61F 2002/4258; A61F 2/4261–2002/4297; A61F 2002/30919; A61F 2/30907; A61F 2/38; A61F 2/3859; A61F 2002/3863; A61F 2/3872; A61F 2002/3895; A61F 2002/30985; A61F 2/30942; A61F 2240/002
See application file for complete search history.

(56) References Cited

U.S. PATENT DOCUMENTS

| | | | | |
|---|---|---|---|---|
| 4,151,615 A | * | 5/1979 | Hall | A61F 2/3877 623/20.19 |
| 5,171,282 A | * | 12/1992 | Pequignot | A61F 2/30907 623/20.35 |
| 5,768,134 A | * | 6/1998 | Swaelens | A61C 13/0004 700/121 |
| 6,002,859 A | * | 12/1999 | DiGioia, III | A61F 2/46 703/11 |
| 6,214,051 B1 | * | 4/2001 | Badorf | A61F 2/3859 623/20.14 |
| 6,712,856 B1 | * | 3/2004 | Carignan | A61B 34/10 623/20.35 |

(Continued)

*Primary Examiner* — Alvin J Stewart
(74) *Attorney, Agent, or Firm* — Armis IP Law, LLC (57) ABSTRACT

A surgical implant for a wrist bone fabricated on a patient-specific basis is based on a combination of the patient's own anatomy and an anatomical ideal from a database of scan data, and provides a patient-specific implant that minimizes spacing tolerance between adjacent bones to allow native cooperation between tightly spaced wrist bones. The three lower skeletal structures in the human wrist, including the trapezium, lunate and scaphoid bones, share a close, integrated geometry with the adjacent arm bones (radius, ulna) and remaining wrist bones. In contrast to conventional approaches that rely on reshaped connective tissue or generically shaped replacements, a patient-specific prosthetic restores the original geometry and spacing between wrist bones, allowing individual bone replacement without removal or fusing to adjacent bones, thus restoring a natural range of movement.

13 Claims, 9 Drawing Sheets

(56) References Cited

U.S. PATENT DOCUMENTS

| | | | |
|---|---|---|---|
| 7,544,209 B2* | 6/2009 | Lotke | A61F 2/3877 623/20.18 |
| 7,833,274 B2* | 11/2010 | Popoola | A61F 2/38 623/20.14 |
| 7,837,739 B2 | 11/2010 | Ogilvie | |
| D655,008 S | 2/2012 | Gannoe et al. | |
| 8,617,242 B2* | 12/2013 | Philipp | B23P 19/04 623/18.11 |
| 8,843,229 B2 | 9/2014 | Vanasse et al. | |
| 9,119,613 B2 | 9/2015 | Gannoe et al. | |
| 9,381,085 B2* | 7/2016 | Axelson, Jr. | A61F 2/30771 |
| 9,622,868 B2* | 4/2017 | Lloyd | A61F 2/3859 |
| 9,655,727 B2* | 5/2017 | Wellings | A61F 2/3877 |
| 9,763,791 B2* | 9/2017 | Lawrynowicz | A61F 2/3609 |
| 10,085,839 B2* | 10/2018 | Wong | A61F 2/30942 |
| 2003/0114936 A1* | 6/2003 | Sherwood | A61F 2/30942 623/23.58 |
| 2003/0216669 A1* | 11/2003 | Lang | A61F 2/30756 600/587 |
| 2004/0133276 A1* | 7/2004 | Lang | A61F 2/32 623/14.12 |
| 2004/0204760 A1* | 10/2004 | Fitz | A61F 2/30756 623/14.12 |
| 2005/0171604 A1* | 8/2005 | Michalow | A61F 2/38 623/14.12 |
| 2006/0004460 A1* | 1/2006 | Engh | A61F 2/38 623/20.21 |
| 2006/0136058 A1* | 6/2006 | Pietrzak | A61F 2/30942 623/13.14 |
| 2007/0100459 A1* | 5/2007 | Rhodes | A61F 2/3877 623/20.19 |
| 2007/0100461 A1* | 5/2007 | Incavo | A61F 2/38 623/20.19 |
| 2007/0100462 A1* | 5/2007 | Lang | A61F 2/38 623/20.29 |
| 2007/0219641 A1* | 9/2007 | Dorr | A61F 2/30767 623/22.42 |
| 2007/0233269 A1* | 10/2007 | Steines | A61B 5/107 623/20.21 |
| 2007/0255288 A1* | 11/2007 | Mahfouz | A61B 5/1075 606/102 |
| 2008/0058945 A1* | 3/2008 | Hajaj | A61F 2/38 623/20.14 |
| 2008/0288081 A1* | 11/2008 | Scrafton | A61F 2/38 623/20.33 |
| 2009/0088846 A1* | 4/2009 | Myung | A61F 2/4241 623/14.12 |
| 2009/0222103 A1* | 9/2009 | Fitz | A61F 2/30942 623/18.11 |
| 2009/0254190 A1 | 10/2009 | Gannoe et al. | |
| 2011/0022179 A1* | 1/2011 | Andriacchi | A61F 2/38 623/20.18 |
| 2011/0035012 A1* | 2/2011 | Linares | A61F 2/30756 623/18.11 |
| 2011/0066243 A1* | 3/2011 | Rivin | A61F 2/3872 623/14.12 |
| 2011/0082548 A1* | 4/2011 | Assell | A61F 2/30756 623/14.12 |
| 2011/0144760 A1* | 6/2011 | Wong | A61F 2/38 623/20.14 |
| 2011/0266265 A1* | 11/2011 | Lang | A61F 2/30756 219/121.72 |
| 2012/0209394 A1* | 8/2012 | Bojarski | A61F 2/38 623/20.32 |
| 2012/0209396 A1* | 8/2012 | Myung | C08G 77/38 623/22.11 |
| 2012/0330429 A1* | 12/2012 | Axelson, Jr. | A61F 2/30771 623/20.19 |
| 2014/0010951 A1* | 1/2014 | Vargas | C23C 16/045 427/2.26 |
| 2014/0025181 A1 | 1/2014 | Vanasse et al. | |
| 2014/0135938 A1* | 5/2014 | Assell | A61F 2/3872 623/20.31 |
| 2014/0316526 A1* | 10/2014 | Grotz | A61L 27/54 623/20.17 |
| 2014/0371863 A1 | 12/2014 | Vanasse et al. | |
| 2015/0297350 A1* | 10/2015 | Robichaud | A61F 2/3859 623/20.32 |
| 2016/0367369 A1* | 12/2016 | Alotaibi | A61F 2/30756 |
| 2017/0079721 A1* | 3/2017 | Zhao | A61F 2/36 |
| 2017/0143495 A1* | 5/2017 | Dunn | A61F 2/30771 |
| 2017/0143501 A1* | 5/2017 | Honigmann | A61F 2/30942 |
| 2017/0202672 A1* | 7/2017 | Persaud | A61L 27/18 |
| 2017/0281355 A1* | 10/2017 | Winslow | A61F 2/30771 |
| 2017/0304056 A1* | 10/2017 | Gaignon | A61L 27/10 |
| 2018/0021138 A1* | 1/2018 | Estes | A61L 27/18 623/16.11 |
| 2018/0028320 A1* | 2/2018 | Forsell | A61F 2/3607 |
| 2018/0064544 A1* | 3/2018 | Grotz | A61L 27/54 |
| 2018/0206995 A1* | 7/2018 | Kang | A61F 2/30756 |
| 2018/0271659 A1* | 9/2018 | Mansmann | A61F 2/30767 |
| 2018/0325683 A1* | 11/2018 | Logan | A61F 2/389 |
| 2019/0076254 A1* | 3/2019 | Essayed | A61F 2/2875 |
| 2019/0099273 A1* | 4/2019 | Servidio | A61F 2/30749 |
| 2019/0110905 A1* | 4/2019 | Cabot | A61B 17/157 |
| 2019/0240030 A1* | 8/2019 | Coulange | A61B 17/72 |
| 2019/0380838 A1* | 12/2019 | Ghodbane | A61F 2/30942 |
| 2020/0030101 A1* | 1/2020 | Eltorai | A61F 2/42 |

* cited by examiner

FIG. 7D (trapezium)

Fig. 8

(lunate)

FIG. 9C

FIG. 9B
(scaphoid)

PATIENT SPECIFIC CARPAL IMPLANT

BACKGROUND

Prosthetic appliances are surgical implants that replace natural skeletal structures in a patient. Natural skeletal structures such as bones, tendons and ligaments can be compromised by age, disease and traumatic injury, as well as other causes. Surgical replacement with an orthopedic implant attempts to duplicate the original bone or skeletal member so that the patient may continue to enjoy mobility and dexterity once provided by healthy skeletal members. Replacement orthopedic implants are particularly beneficial in the wrist, as the natural skeletal structures include an arrangement of small, interconnected bones having specific irregular shapes that mesh and cooperate with other adjacent bones. Modern developments in CAD/CAM (computer aided design/computer aided manufacturing) has facilitated fabrication of these complex shapes.

Since the wrist is not a single-axis joint with collateral ligaments guiding a unidirectional arc of motion, the unconstrained wrist seldom rotates in a pure flexion-extension or radial-ulnar deviation mode, due to multiple degrees of freedom. In fact, most activities of daily living (using a hammer, fishing, bouncing a ball, or lifting heavy objects) involve an oblique type of wrist motion, from extension-radial deviation to flexion-ulnar deviation, as in a so-called "dart-throwing" plane of motion.

The human wrist helps to place the hand in optimal positions to perform a variety of tasks. For this reason, it is vital for hand function. When the wrist is degraded by disease or injury, hand function is compromised. As the wrist is a complex collection of multiple articulations, its anatomy and function is also complex.

SUMMARY

A wrist bone replacement prosthesis fabricated on a patient-specific basis based on a combination of the patient's own anatomy and an anatomical ideal from a database of scan data results in a patient-specific implant that minimizes spacing tolerance between adjacent bones to allow native cooperation between tightly spaced wrist bones. The three lower skeletal structures in the human wrist, including the trapezium, lunate and scaphoid bones, share a close, integrated geometry with the adjacent arm bones (radius, ulna) and remaining wrist bones. In contrast to conventional approaches that rely on reshaped connective tissue or generically shaped replacements, a patient-specific prosthetic restores the original geometry and spacing between wrist bones, allowing individual bone replacement without removal or fusing to adjacent bones, thus restoring a natural range of movement.

Configurations herein are based, in part, on the observation that orthopedic wrist procedures involve management of an integrated bone structure around the tightly coupled wrist bones. These skeletal structures form a cooperative network of solid bone and connective tissue having complementary shapes that operate at a cohesive whole. Unfortunately, conventional approaches to surgical wrist procedures suffer from the shortcoming that bones are often replaced with prosthetic approximations and/or tightly attached or fused to adjacent bone members, or requires group removal of multiple bones, including healthy structures, to accommodate a repair. This anatomical sub-ideal often compromises the resulting range of motion. Accordingly, configurations herein substantially overcome the above-described shortcomings by providing a patient-specific implant based on scans of the native anatomy that replicates the shape, contour and size of the native bone being replaced, rather than relying on prefabricated shape and size approximations offered by conventional prosthetics.

Configurations disclosed herein provide a method of fabricating a wrist bone implant, including receiving an identification of a skeletal member for replacement, in which the skeletal member is a wrist bone in close proximity to adjacent wrist bones. Scan data indicative of the identified skeletal member is received or gathered, such that the received scan data includes contralateral scan data of a healthy bone from the same patient, scans indicative of an anatomical ideal from a database of scan data, and/or ipsilateral scan data of a prior time of the identified skeletal member. A 3-dimensional imaging and rendering application coalesces the received scan data to generate a surgical model based on anatomical features of a healthy skeletal member, and renders a replacement prosthesis from the generated surgical model. The replacement prosthesis is adapted for unitary replacement in proximity to the adjacent wrist bones.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example of a surgical implant fabrication and corresponding implantation procedure that fabricates the unitary model of a plurality of intercalary bone structures such as in a proximal carpal row of a wrist. The human wrist is generally acknowledged to include 8 bones between the arm (radius, ulna), and the digits. Of these, bones adjacent to the arm (trapezium, lunate and scaphoid) are often the subject of replacement therapy.

Orthopedic wrist implants are expected to benefit a diverse array of patient. First and foremost, patients suffering from thumb CMC arthritis, Kienbock's disease and scaphoid non-union fracture, none of which enjoy proven or long lasting treatments, can have an anatomically accurate replacement of the damaged bone designed specifically for them. Such conformity translates to a better perceived fit, shorter recovery time and improved osteo-integration. Surgeons benefit in the way of reduced infection risks and higher satisfaction among their patients. Providers have the benefit of reduced inventory costs, higher throughput and implants on demand based on individual, patient-specific fabrication. Depicted below is a system, method and apparatus for generating a patient-specific prosthetic implant based on the anatomy of the patient.

Figure 1:
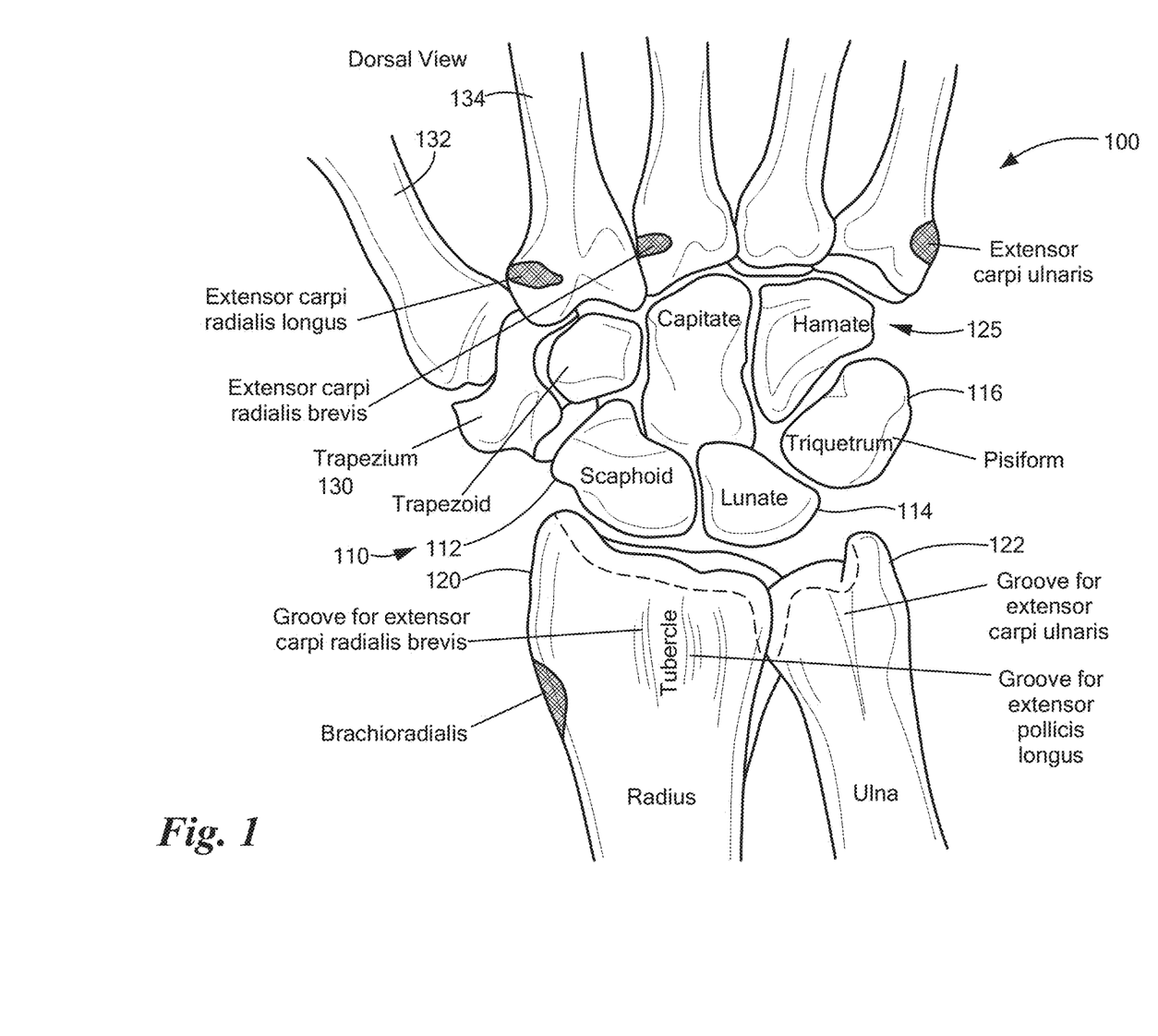
FIG. 1 is an anatomical diagram of a wrist suitable for depicting usage of the approach disclosed herein.

FIG. 1 is an anatomical diagram of a wrist suitable for depicting usage of the approach disclosed herein. The wrist anatomy is formed by a complex structure of skeletal and connective members that interoperate as a cohesive whole. The bones generally include complex curves and valleys that are not readily approximated by conventional geometric shapes. Some of the bones are positionally fixed substantially by adjacent bones in an intercalary arrangement. Accordingly, replacement of individual skeletal members (bones) can be highly dependent on adjacent skeletal members and connective tissue.

Configurations herein depict a system, method and apparatus for creating implants from images of patient scans. The disclosed approach overcomes the shortcomings of the current surgical treatment, by making the implant patient-specific. A scan is taken of the patient's opposite side to serve as an ideal mirror-image non-injured model. This contralateral image is reconstructed to serve as the basis for the novel implant design. The implant is 3D printed the using polymers, metal, or other biocompatible materials. An implant sized and shaped to match the skeletal member it is replacing is then delivered to the surgeon before the surgery.

The prosthetic replacement of individual bones permits the adjacent wrist bones to remain undisturbed. By receiving scan data indicative of the identified skeletal member from several sources, and selectively partitioning the scan data to separate "healthy" segments from compromised areas, a coalesced image of a healthy, native bone is 3D printed to have the shape and size of the native bone it replaces. The scan sources include contralateral scans of the patient, anatomical ideals from a database, and ipsilateral scans of the same bone in a pre-disease state.

Contralateral scans of the patient can be taken as an accurate representation of a healthy skeletal structure. Such a contralateral scan is based on a corresponding skeletal member on an opposed side from the skeletal member for replacement. In most cases, the opposed side (e.g. right or left) of complementary skeletal structures define mirror images of the other. When one side is compromised by disease, the opposite side, if healthy, represents an inversion of the diseased side. By taking contralateral scan data and performing processing to invert the image, a patient-specific replacement is derived.

When either the opposed side is not healthy, or has notable differences, scan data may be available of the actual diseased structure. Ipsilateral scans may be employed that result from previous scans taken of the skeletal member for replacement at a time prior to compromising symptoms.

Another source of scan data is to retrieve an anatomical ideal from a database of scan data gathered from healthy skeletal members and arranged by anatomical features. A database of prosthetic image data may be gathered from research, prior procedures, and known characteristics. An ideal image approximating a shape and size of the patient's own structures may be used to supplement for segments of the prosthesis that are incomplete and/or have identifiable defects. By combining and coalescing image data from multiple bone segments, an exact or close match to the undiseased trapezium, lunate or scaphoid is imaged.

The trapeziometacarpal joint is one of the most common sites of osteoarthritis in the human body, particularly in postmenopausal women. Multiple surgical techniques exist to address this problem, including arthrodesis, implant arthroplasty, and trapeziectomy with or without ligament reconstruction/tendon interposition. A trapeziectomy with ligament reconstruction is considered to be a preferred approach for treatment of trapeziometacarpal osteoarthritis, but disadvantages of this procedure include proximal migration of the thumb metacarpal after trapezial resection, resulting in reduced pinch strength.

The most common procedure, however, has been a trapeziectomy with a ligament reconstruction tendon interposition. During this procedure the arthritic trapezium is excised to remove arthritic joint surfaces, the anterior oblique ligament is reconstructed to restore thumb metacarpal stability and prevent axial shortening, and a fascial interposition is performed to reduce the likelihood of impingement between neighboring bones.

Conventional approaches, therefore, rely on either a harvested reshaped tendon or a metal prosthetic of a fixed size and shape. A harvested length of connective tissue, such as a tendon or ligament, is reshaped by rolling and/or compressing into an insertable shape to replace the removed trapezium. The resulting replacement tends to be ball-shaped and falls short of an anatomical ideal.

Other approaches employ non-reactive metals to form an implant. Metalworking to fabricate the replacement requires exotic materials and sophisticated manufacturing, increasing cost. Also, the resulting implant is generally limited to selection of several sizes, such as small, medium and large, and is not based on the unique shape of the bone it is replacing. Nonreactive metals often employed in forming the pre-fabricated replacement are usually only formed in a limited number of sizes. This forces a nearest fit selection without regard to gaps or tolerances to adjacent bones.

Referring to FIG. 1, in a patient wrist 100 includes a proximal carpal row (PCR) 110 defined by three adjacent bones: the scaphoid 112, lunate 114 and triquetrum 116. The proximal carpal row 110 resides adjacent the distal radius 120 and ulna 122, and abuts the distal carpal row 125 on a side nearest the digits (fingers). A second metacarpal 134 is adjacent the thumb, or first metacarpal 132, and will be discussed further below. As can be seen in the dorsal (opposite of palm side) wrist view of FIG. 1, the scaphoid 112, lunate 114 and triquetrum 116 are tightly disposed in position between the radius 120/ulna 122 at the end of the arm on one side and the distal carpal row 125 on the opposed side nearest the fingers. The trapezium 130 sits at the base of the thumb 132. These adjacent bones "fit" almost as if pieces of a jigsaw puzzle, held in place by surrounding bones and other soft tissue such as ligaments and muscles. In various configurations, the disclosed approach is operable for use with adjacent skeletal structures that are intercalary bone structures secured by proximate, disconnected skeletal structures.

Figure 2:
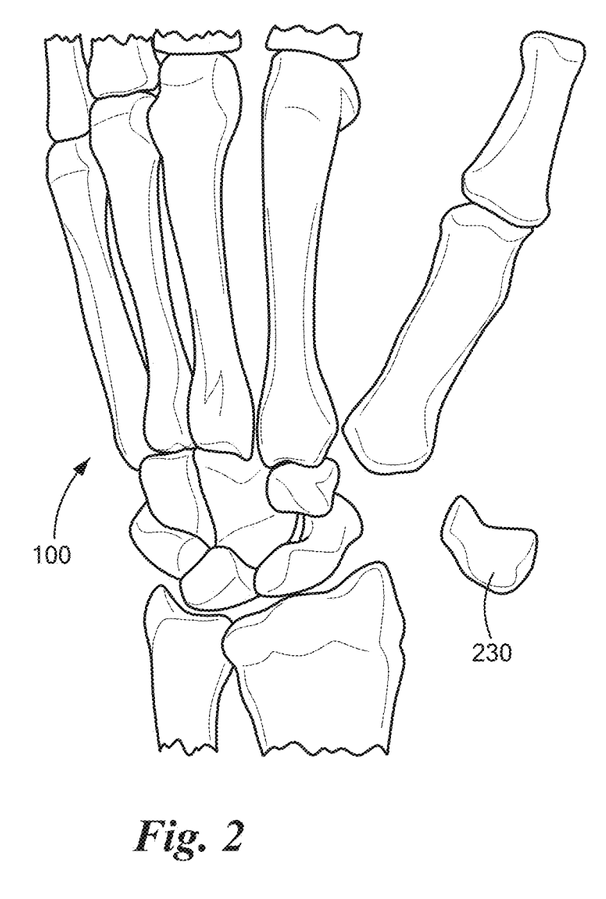
FIG. 2 is a diagram of a trapezium replacement procedure.
Figure 3:
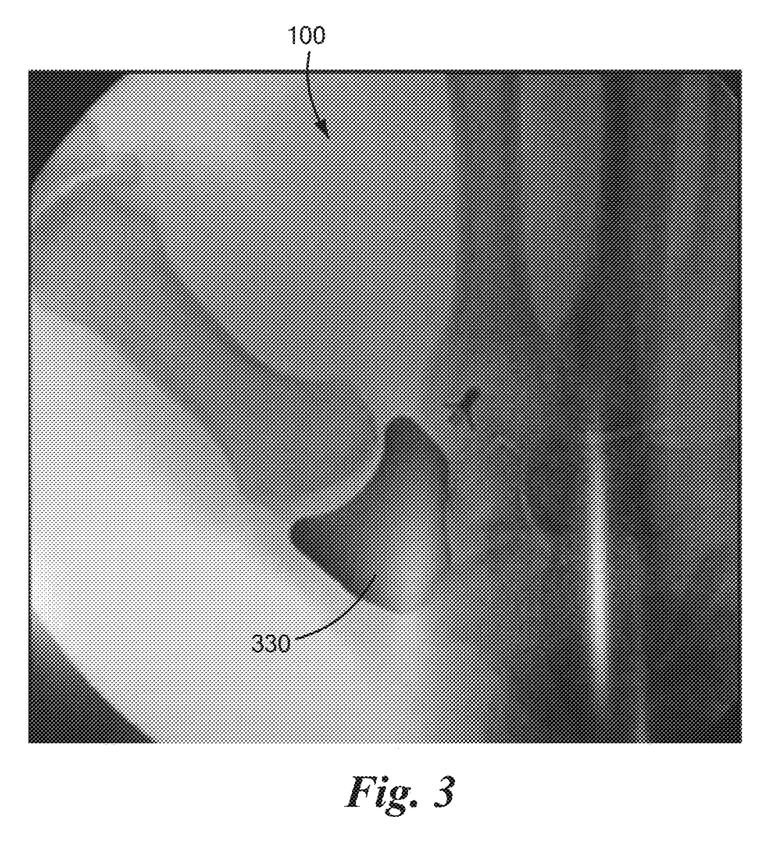
FIG. 3 shows a finished trapezium replacement following the procedure of FIG. 2.

FIGS. 2 and 3 are diagrams of a trapezium replacement procedure. In the patient wrist 100, a fabricated trapezium prosthetic will replace the removed, native trapezium 230 at the base of the first metacarpal 132.

FIG. 3 shows a finished trapezium replacement following the procedure of FIG. 2. The skeletal member for replacement is a trapezium and accordingly, the replacement prosthesis 330 is non-geometrically shaped and is based on a natural bone shape. Conventional approaches to 3D rendering encounter difficulties with irregular shapes, and are therefore based on precise image scans and rendering materials to avoid distortion from the intended scan-based image to the actual rendered prosthesis 330. By matching both the size and shape of the native bone structure, the patient-specific prosthetic results in fewer gaps and tolerances between the native skeletal structure and more closely approximates the bone it is replacing.

Figure 4:
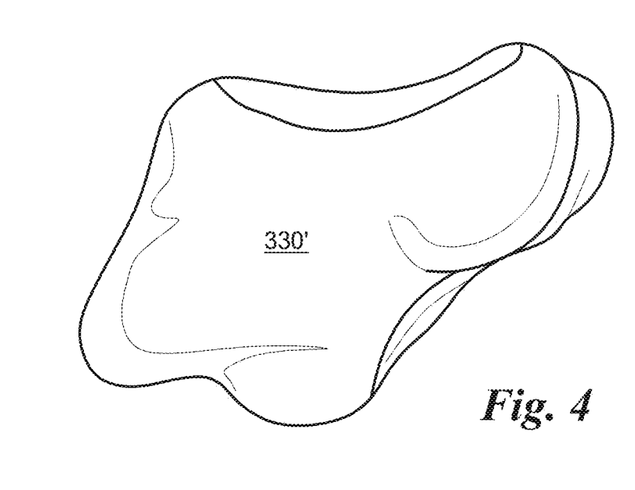
FIG. 4 shows the patient-specific implant employed in the replacement of FIG. 3.
Figure 8:
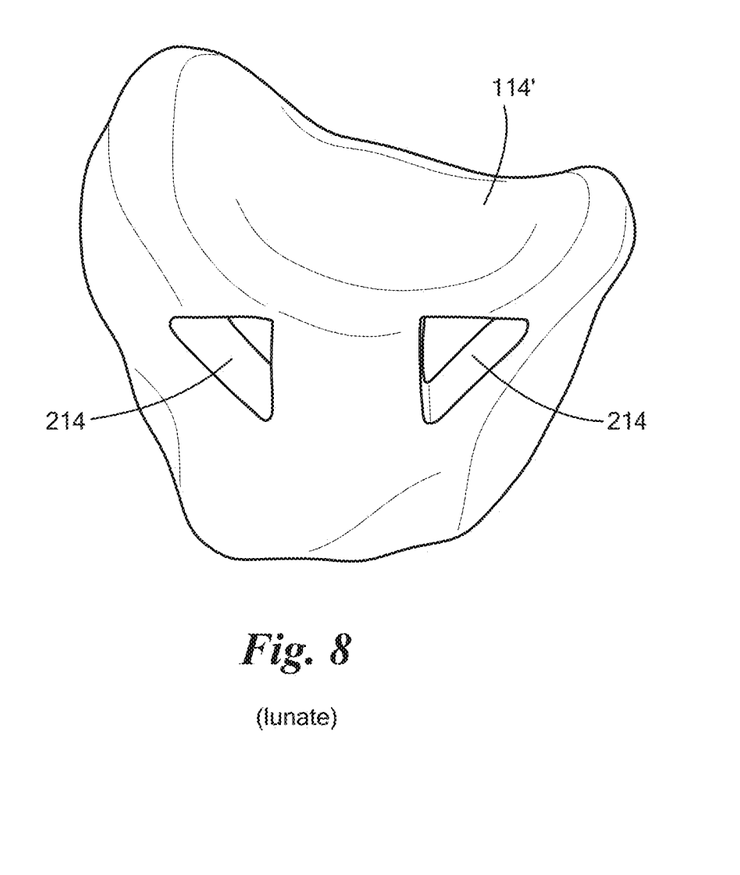
Figure 9A:
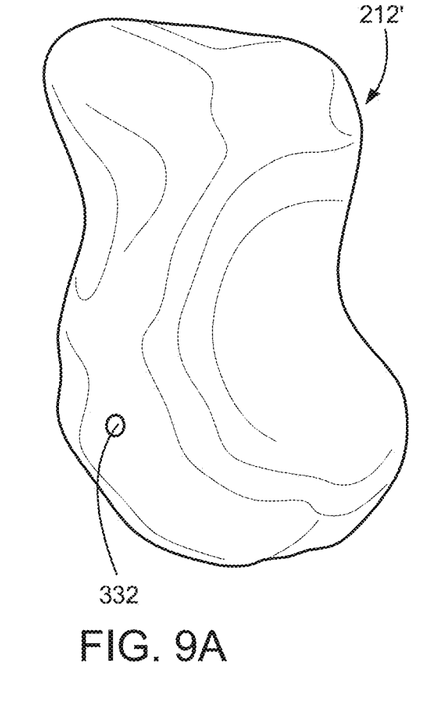
Figure 9B:
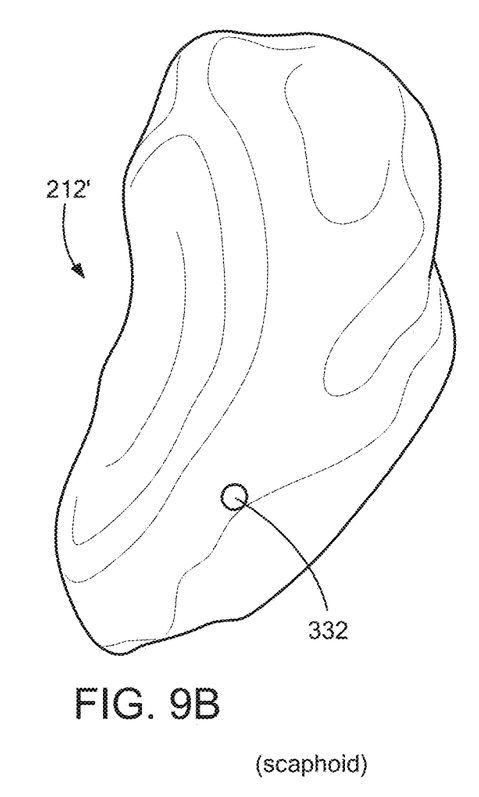
Figure 9C:
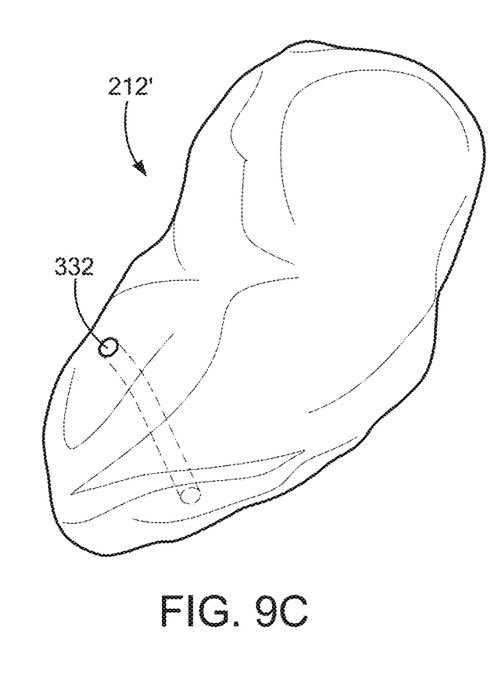
Figure 10A:
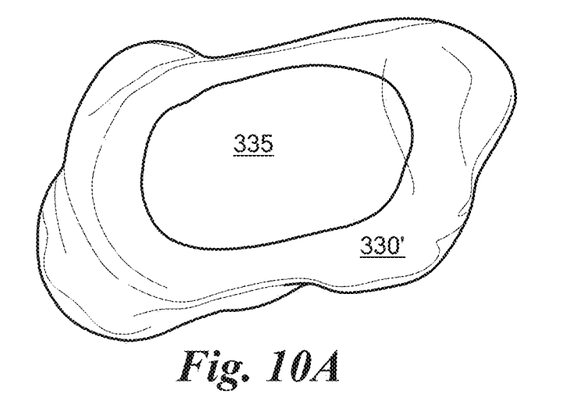
FIGS. 10A-E and 11A-H show the trapezium and lunate with caps that help them articulate with other carpal bones.
Figure 10B:
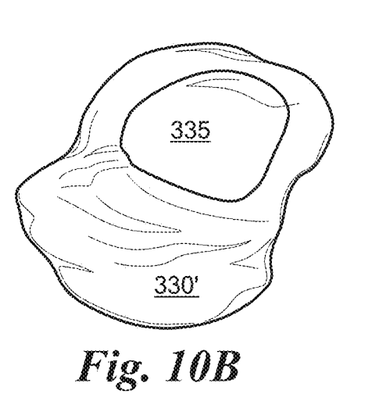
Figure 10C:
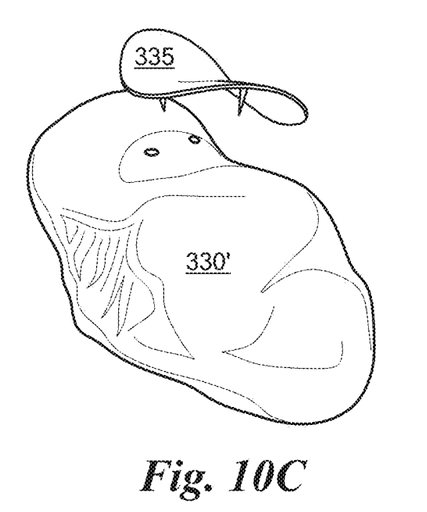
Figure 10D:
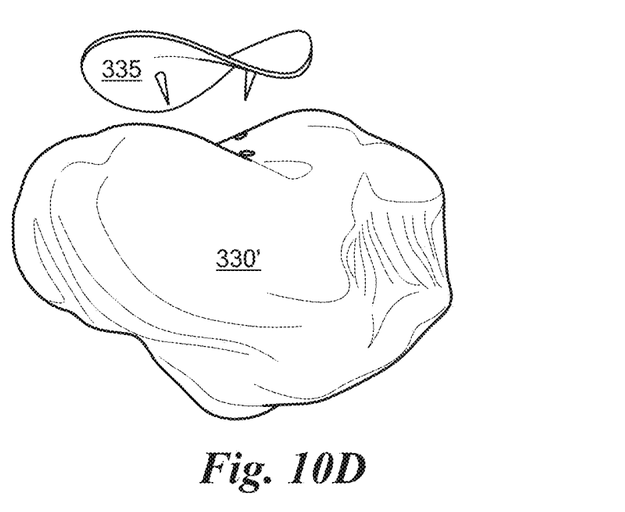
Figure 10E:
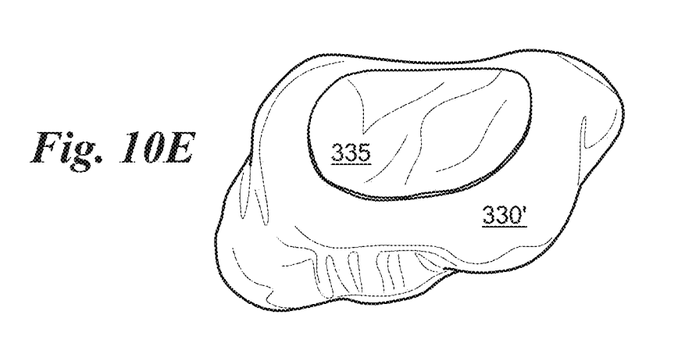
Figure 11A:
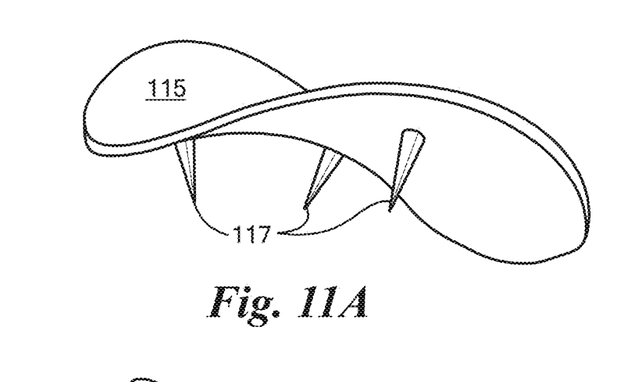
Figure 11B:
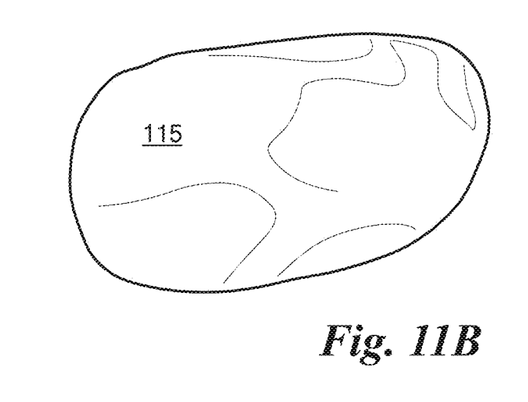
Figure 11C:
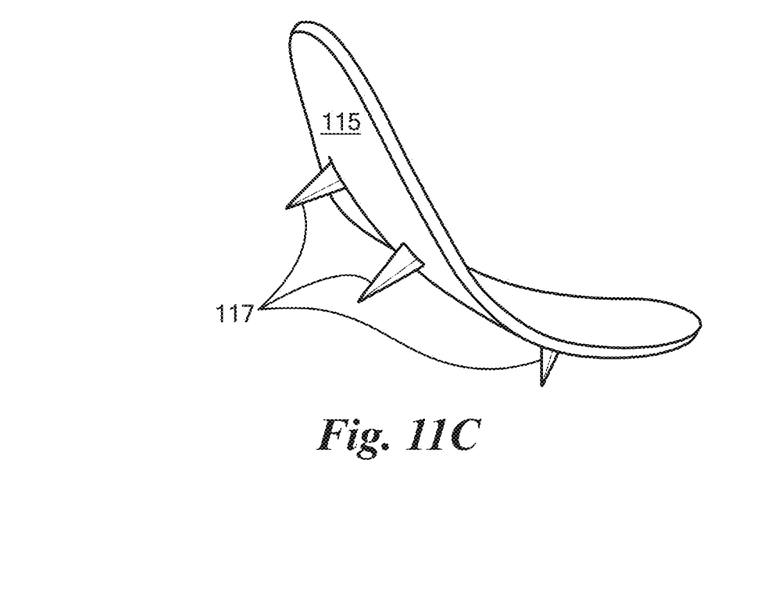
Figure 11D:
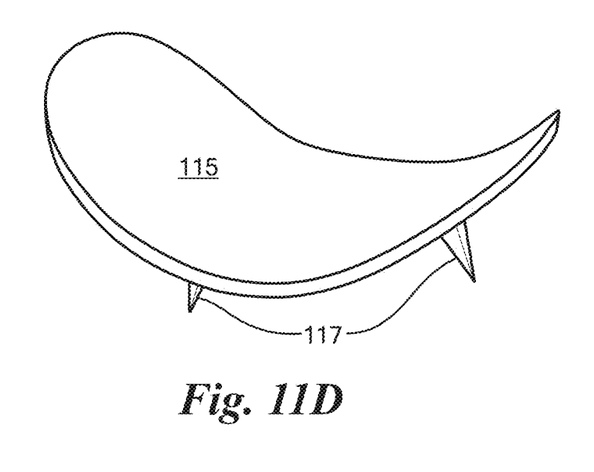
Figure 11E:
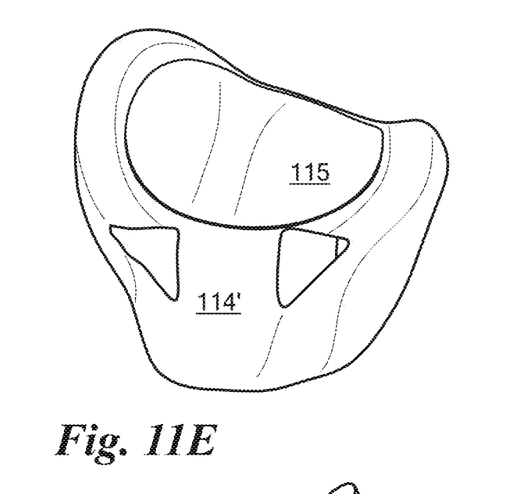
Figure 11F:
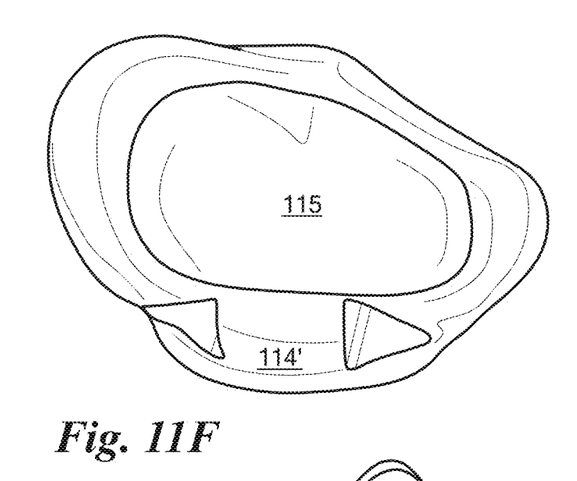
Figure 11G:
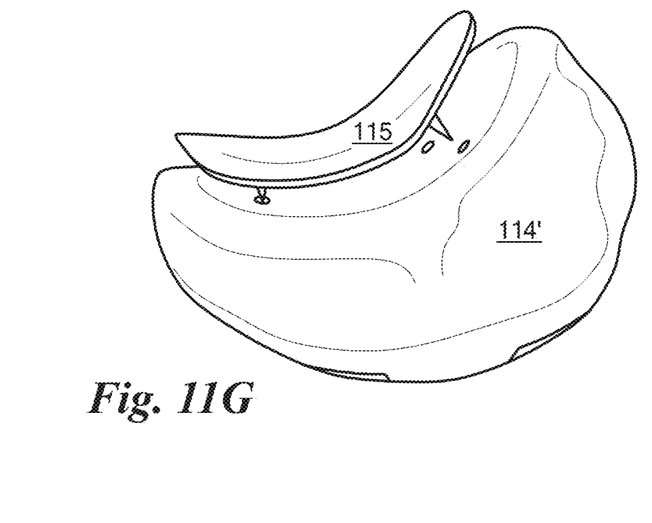
Figure 11H:
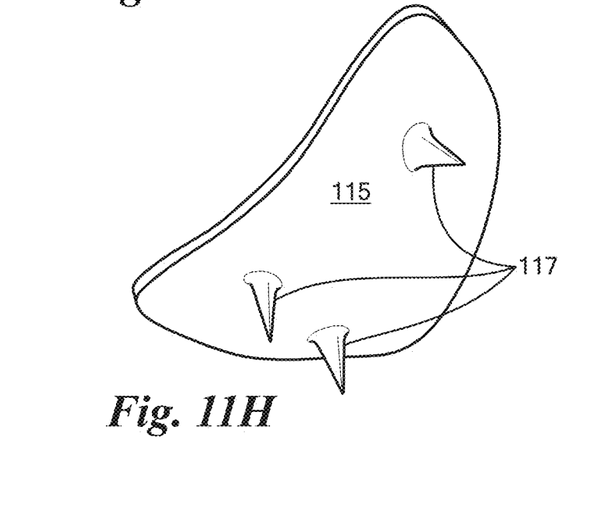

FIG. 4 shows an alternate view 330' of the patient-specific implant 330 employed in the replacement of FIG. 3. Certain regions may employ a cap or more load-bearing material than the remaining structure in regions of frictional contact, shown in greater detail below in FIGS. 10, 11 and 12. Surgical attachments and tethers may be added at any suitable locations, such as tunnels for tethered attachment (sutures) or rigid attachment such as bone anchors and screws. As with the overall shape, tunnels and anchor holes may be formed in patient-specific, optimal locations based on surgical preferences, as shown in FIGS. 7, 8 and 9.

Figure 5:
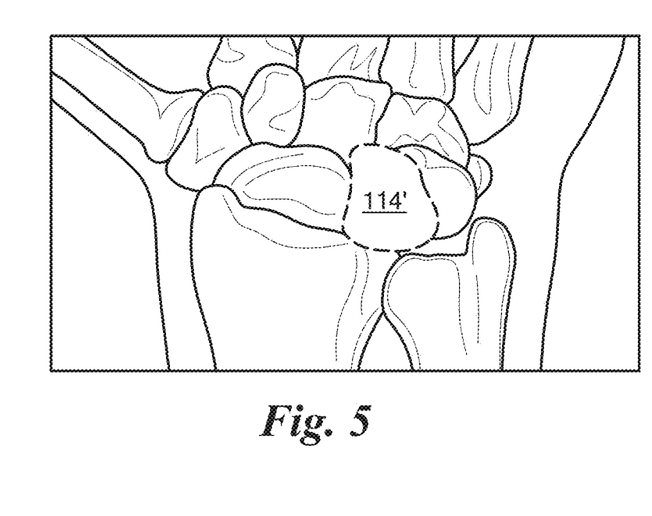
FIG. 5 shows a patient-specific implant for a lunate.

FIG. 5 shows a patient-specific implant for a lunate bone 114. A particularly common ailment manifested by avascular necrosis of the lunate is Kienböck's disease. Kienböck's disease can ultimately progress to complete collapse and fragmentation, rendering the lunate unsalvageable. By way of background, natural history studies of early-stage Kienböck's disease do not indicate that progression to higher stages is a certainty or that intervention during the early stages necessarily changes the final outcome. Once collapse has begun, progression to further collapse and eventual fragmentation is expected. Magnetic resonance imaging (MRI) is frequently used in early-stage disease to confirm the diagnosis when plain radiographs are equivocal. There are two distinguishing features that identify an unsalvageable lunate; both are best delineated on computed tomography (CT) scan. A lunate cannot be salvaged if the hyaline cartilage has delaminated from the underlying subchondral bone, or if the lunate has already fragmented into multiple pieces.

Many conventional approaches attempt to restore vascular communication with a diseased lunate. Depending on disease progression, the ultimate treatment selection may involve revascularization, fusion or incision. While many medical processes benefit from sophisticated scan data such as magnetic resonance imaging (MRI), MRI offers little help in prognosis and treatment planning for lunate replacement. The most commonly used Stahl/Lichtman classification scheme is based on plain radiographs and does not distinguish a lunate that can be salvaged from one that cannot. Many stage IIIB lunates can be salvaged with vascularized bone grafting, avoiding irreversible anatomic modification of wrist structure. There are two distinguishing features that identify an unsalvageable lunate; both are best delineated on computed tomography (CT) scan.

In the configurations herein, when the skeletal member for replacement is a lunate, a replacement prosthesis 114' is shaped based on a pre-disease state of the skeletal member for replacement. Conventional approaches attempt invasive micro-vascular approaches to restore bloodflow to a necrotic lunate. The patient-specific lunate prosthesis mitigates geometry imprecisions that allow the prosthetic lunate to integrate with the adjacent healthy bones, specifically the trapezium, scaphoid and triquetrum.

Figure 6:
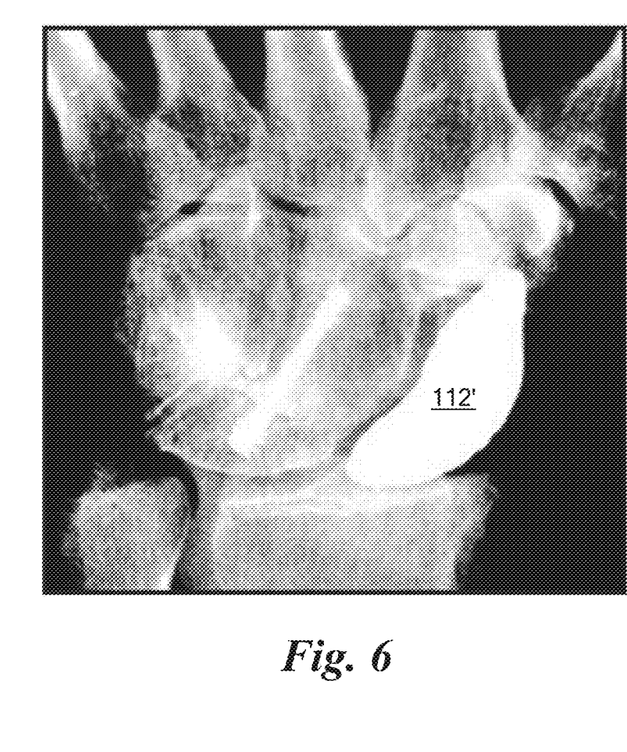
FIG. 6 shows a scaphoid implant location.
Figure 7A:
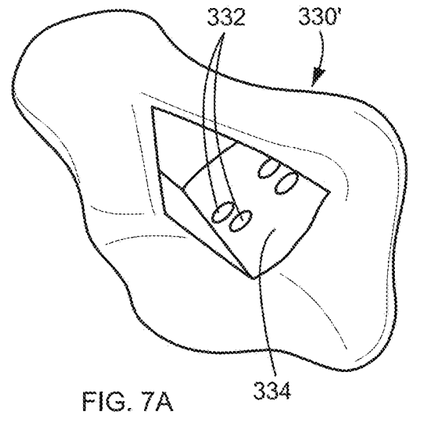
FIGS. 7A-7D, 8 and 9A-9C show the trapezium, lunate and scaphoid implants with the required screw/suture holes for necessary fixations.
Figure 7B:
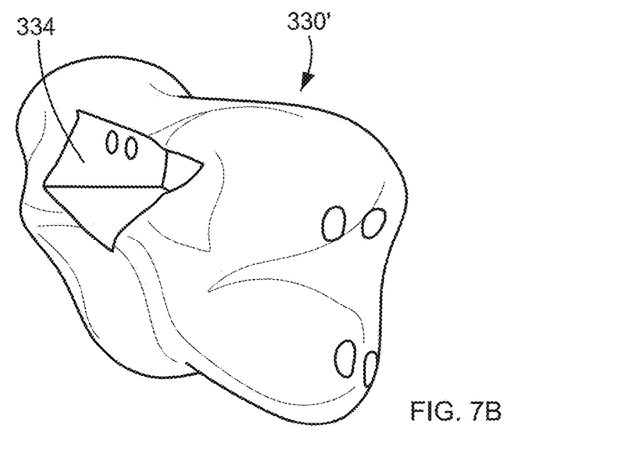
Figure 7C:
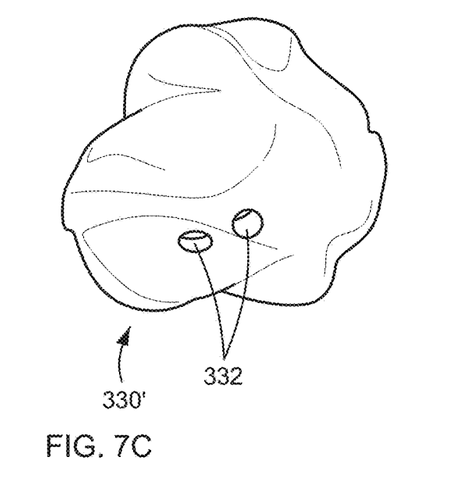
Figure 7D:
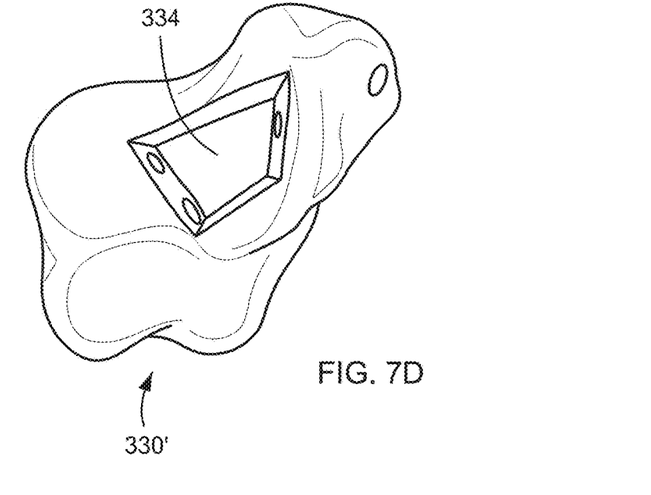

FIG. 6 shows a scaphoid implant 112' location. The scaphoid bone 112 is adjacent to the lunate in the eight small bones that comprise the wrist joint. The two rows of small wrist bones act together to allow the wide variety of wrist positions and motions that are often taken for granted. The scaphoid bone 112 spans or links these two rows together and, therefore has a special role in wrist stability and coordinating wrist motion. The scaphoid bone is vulnerable to fracture because of its position within the wrist and its role in wrist function. When the scaphoid bone is broken, it may not heal properly because it has a very fragile blood supply. Scaphoid fractures that do not heal are referred to as a scaphoid non-union. Ultimately, scaphoid non-unions can lead to loss of wrist motion and eventual wrist arthritis.

The pitfalls of treatment of scaphoid fractures are very common in the current practice: the well-known sequelae are nonunion, necrosis of the fragments, carpal biomechanical changes leading to scaphoid nonunion advanced collapse arthritis and ultimately, severe degenerative arthritis of the entire radiocarpal and intercarpal joints.

In the case of a deteriorated scaphoid, conventional surgical methods tend towards a prosthetic implant fused to adjacent bones, due to an inability to generate a prosthetic in sufficient alignment with the current structures. Alternatively, the entire proximal carpal row (PCR) may be replaced. This results in a suboptimal repair as the range of motion is often compromised. A patient-specific scaphoid implant results in a closely fit prosthetic that integrates with the existing skeletal structure to avoid replacement of healthy, adjacent structures merely to maintain an acceptable bone "fit."

Accordingly, it is beneficial to generate a prosthetic for replacing only the scaphoid, rather than fusing to or replacing adjacent bones. The disclosed approach for a patient-specific prosthetic is applied such that the skeletal member for replacement is a scaphoid and the replacement prosthesis is adapted to be disposed between the native adjacent wrist bones. A scaphoid total replacement can be considered when three conditions are evident in preoperative clinical evaluation of scaphoid necrosis:

i) scaphoid destruction, unsuitable for a reconstruction with grafting techniques;

ii) good wrist stability and absence of a scaphoid non-union advanced collapse (SNAC) wrist condition, as demonstrated by carpal height and radiolunate angle measurements; and iii) absence of degenerative changes in the radial scaphoid facet and/or other carpal bones.

Implementation of the implants takes the form of an imaging and 3-dimensional printing application that define a fabrication apparatus for forming a wrist bone implant. An application receives an identification of a skeletal member for replacement, the skeletal member being a wrist bone in close proximity to adjacent wrist bones, and an interface to an imaging device for receiving scan data indicative of the identified skeletal member. Scanning and imaging devices such as MRI and CT scans employ imaging formats adapted to be read and manipulated by the application. The received scan data includes one or more of:

i) contralateral scan data of a healthy bone from the same patient, ii) scans indicative of an anatomical ideal from a database of scan data, and iii) ipsilateral scan data of a prior time of the identified skeletal member.

The application includes imaging logic in the configured to coalesce the received scan data to generate a surgical model based on anatomical features of a healthy skeletal member, in effect taking the preferred portions or segments from the available scans and reassembling into a near-healthy combination. An interface to a 3-dimensional printing device is configured to render a replacement prosthesis from the generated surgical model, such that the replacement prosthesis adapted for unitary replacement in proximity to the adjacent wrist bones. Biocompatible print mediums allow prosthetic implant generation using extrusion on a 3-D printer.

FIGS. 7A-7D, 8 and 9A-9D show the trapezium, lunate and scaphoid implants with the required screw/suture holes for necessary fixations. Referring to FIGS. 7A-9C, the lunate, scaphoid and trapezium are among the carpal bones in the human hand as disclosed above. The trapezium implant 330, distinguished by a deep groove on the anterior surface, articulates with the scaphoid, trapezoid as well as the bases of the first and second metacarpals. Suture tunnels 332 and voids 334 aid in surgical attachment. The lunate implant 114' includes triangular voids 214 The boat-shaped scaphoid implant 212' is the largest of the proximal row bones and articulates with the radius, trapezoid, trapezium, lunate and capitate. Suture tunnels 332 facilitate attachment.

Over time, articulations of these cooperative implants can result in a wear and tear of the bones, compromising their performance as well as endangering the health of the patient. The 3D printed customized lunate, scaphoid and trapezium bone offerings by Orthopedix, assignee of the claimed approach, intended to replicate the anatomical functions of their natural counterparts including their various articulations, have been specifically engineered to minimize degradation and wear. This is accomplished by inserting a cap head over the articulating surfaces of the implants thereby reducing friction between the surfaces, discussed further below. The implants have holes either drilled into them or designed as part of the printing/fabrication process. The (cap) head is held in place by means of inserts (can be anywhere between one, two or three depending upon the requirement) protruding from underneath the cap, which can fit into the holes and keep the head firmly in place.

FIGS. 10A-E and 11A-H show various views of the trapezium, lunate and scaphoid with caps that help them articulate with other carpal bones. Any of the implants disclosed herein can be made out of materials that are biocompatible and 3D printable, including Cobalt-chromium alloys (Co—Cr), Titanium or Titanium alloys, Poly ether ketone (PEEK), Poly ether ketone (PEKK) or even Zirconium alloys. Co—Cr alloys are hard, tough, corrosion-resistant and biocompatible. One potential area of concern with these alloys is the release of metal ions into the patient thereby causing allergic reactions. Pure titanium may be used where high strength is not a priority. Titanium alloys are biocompatible, have low density and elasticity. This means that these implants resemble natural joint movements and thereby reduce bone resorption and atrophy. Medical grade PEEK implants are very bone friendly, wear resistant, have low friction coefficients, excellent osseointegration and are much more compatible with diagnostic imaging than most metal implants. However, their high cost might be a prohibitive factor.

Surface caps applied in areas of maximum strain and/or abrasion fortify the structure to absorb the heightened forces. FIGS. 10A-10E show trapezium caps 335 attached to the trapezium implant 330'. caps 115. FIGS. 11A-11H show lunate caps 115 attached to the lunate implant 114'. Anchors 117 or similar protrusions may be employed for attachment.

The caps on the other hand, could be manufactured out of pyrocarbon, a specific form of carbon tailored for durability and biocompatibility. It also exhibits favorable wear characteristics and fatigue endurance. For instance, after cyclical testing to 5,000,000 cycles, PyroCarbon demonstrated minimal wear into cortical bone (bovine). Other materials exhibited extensive bone wear at 375,000 cycles (Co—Cr), 50,000-75,000 cycles (Ti) and 25,000 cycles with Zirconia. The elastic modulus of pyrocarbon is quite similar to cortical bone thereby resulting in biomechanical compatibility with bone. This means that pyrocarbon can transfer loads from implant to bone quite effectively, even more so than many surgical grade metals. This reduces stress shielding and potential bone resorption. Most importantly, pyrocarbon's low surface friction can help preserve cartilage. In conventional approaches, a study of cartilage wear in 45 canine acetabula was performed using both pyrocarbon and metal alloy hip prostheses. Pyrocarbon showed remarkably less wear damage to cartilage. After 18 months, cartilage articulating with PyroCarbon exhibited a 92% survivorship probability compared to a 20% cartilage survivorship with metallic alloys.

In a particular configuration, the implant is employed in a surgical replacement according to the following procedure.

Step I: CT scan of bilateral forearm: This CT scanning protocol consists of a localizer and a detailed axial scan of the (bilateral) forearm. The scan quality (with clear bony edges and details) is critical to the production of accurate patient-specific implant. Bilateral imaging can be accomplished with a single acquisition.

Step II: CT scan post-processing: The CT scan of the wrist is post processed to create DICOM files. These DICOM files will serve as a basis for 3D modeling of the implant.

Step III: CT scan to 3D reconstruction: The DICOM files are processed to create 3D representations of the patient's anatomy.

Step IV: Segmentation of reconstructed 3D model: Segmentation of the desired region (carpal bones) is performed using advanced segmentation toolbox in Mimics.

Step V: Identifying and segmentation of required carpal bones: Carpal row bones Scaphoid, Lunate or Trapezium are identified and segmented for 3D measurements which leads to anatomical landmark points for the optimal designing of the replacement.

Step VI: Designing the Implant: The replacement is designed using image processing techniques.

Step VII: Mirror Image conversion: To treat the diseased wrist, the healthy side of the wrist will undergo STEP III to VI. The resulting carpal replacement design is then converted into a mirror image to match the anatomy of the diseased wrist.

Step VIII: Preparing the model for print/rendering: The implant design file is then converted into a stl (stereolithography) file and uploaded to a 3D printer that fabricates the replacement using a desired material.

Those skilled in the art should readily appreciate that the programs and methods defined herein are deliverable to a user processing and rendering device in many forms, including but not limited to a) information permanently stored on non-writeable storage media such as ROM devices, b) information alterably stored on writable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of fabricating a wrist bone implant, comprising:
   receiving an identification of a skeletal member for replacement, the skeletal member being a wrist bone in close proximity to adjacent wrist bones;
   receiving scan data indicative of the identified skeletal member, the received scan data including:
   i) contralateral scan data of a healthy bone from the same patient;
   ii) scans indicative of an anatomical ideal from a database of scan data;
   iii) ipsilateral scan data of a prior time of the identified skeletal member;
   coalescing the received scan data to generate a surgical model based on anatomical features of a healthy skeletal member; and
   rendering a replacement prosthesis from the generated surgical model, the replacement prosthesis adapted for unitary replacement in proximity to the adjacent wrist bones,
   wherein the skeletal member for replacement is a trapezium and the replacement prosthesis is non-geometrically shaped and is based on a natural bone shape, the replacement prosthesis including caps on articulating surfaces to minimize friction against surrounding bones, each cap being held in place by means of inserts that fit into holes on the surface of the prosthesis.

2. The method of claim 1 wherein the adjacent wrist bones remain undisturbed.

3. The method of claim 1 wherein the ipsilateral scans result from previous scans taken of the skeletal member for replacement at a time prior to compromising symptoms.

4. The method of claim 1 further comprising retrieving the anatomical ideal from a database of scan data gathered from healthy skeletal members and arranged by anatomical features.

5. The method of claim 1 wherein the contralateral scan data is based on a corresponding skeletal member on an opposed side from the skeletal member for replacement.

6. A method of fabricating a wrist bone implant, comprising:
   receiving an identification of a skeletal member for replacement, the skeletal member being a wrist bone in close proximity to adjacent wrist bones;
   receiving scan data indicative of the identified skeletal member, the received scan data including:
   i) contralateral scan data of a healthy bone from the same patient;
   ii) scans indicative of an anatomical ideal from a database of scan data;
   iii) ipsilateral scan data of a prior time of the identified skeletal member;
   coalescing the received scan data to generate a surgical model based on anatomical features of a healthy skeletal member; and
   rendering a replacement prosthesis from the generated surgical model, the replacement prosthesis adapted for unitary replacement in proximity to the adjacent wrist bones,
   wherein the skeletal member for replacement is a lunate and the replacement prosthesis is shaped based on a pre-disease state of the skeletal member for replacement, the replacement prosthesis including caps on articulating surfaces to minimize friction against surrounding bones, each cap held in place by means of inserts that fit into holes on the surface of the prosthesis.

7. The method of claim 1 wherein the skeletal member for replacement includes a scaphoid and the replacement prosthesis is adapted to be disposed between the adjacent wrist bones the replacement prosthesis including caps on articulating surfaces to minimize friction against surrounding bones, the cap held in place by means of inserts that fit into holes on the surface of the prosthesis.

8. A fabrication apparatus for forming a wrist bone implant, comprising:
   an application for receiving an identification of a skeletal member for replacement, the skeletal member being a wrist bone in close proximity to adjacent wrist bones;
   an interface to an imaging device for receiving scan data indicative of the identified skeletal member, the received scan data including:
   i) contralateral scan data of a healthy bone from the same patient;
   ii) scans indicative of an anatomical ideal from a database of scan data;
   iii) ipsilateral scan data of a prior time of the identified skeletal member;
   imaging logic in the application configured to coalesce the received scan data to generate a surgical model based on anatomical features of a healthy skeletal member; and
   an interface to a 3-dimensional printing device configured to render a replacement prosthesis from the generated surgical model, the replacement prosthesis adapted for unitary replacement in proximity to the adjacent wrist bones,
   wherein the skeletal member for replacement is a scaphoid and the replacement prosthesis is adapted to be disposed between the adjacent wrist bones the replacement prosthesis including caps on articulating surfaces to minimize friction against surrounding bones, each cap held in place by means of inserts that fit into holes on the surface of the prosthesis.

9. The apparatus of claim 8 wherein the ipsilateral scans result from previous scans taken of the skeletal member for replacement at a time prior to compromising symptoms.

10. The apparatus of claim 8 further comprising an interface to the anatomical ideal from a database of scan data gathered from healthy skeletal members and arranged by anatomical features.

11. The apparatus of claim 8 wherein the contralateral scan data is based on a corresponding skeletal member on an opposed side from the skeletal member for replacement.

12. The apparatus of claim 8 wherein the skeletal member for replacement includes a trapezium and the replacement prosthesis is non-geometrically shaped and is based on a natural bone shape, the replacement prosthesis including caps on articulating surfaces to minimize friction against surrounding bones, the cap being held in place by means of inserts that fit into holes on the surface of the prosthesis.

13. The apparatus of claim 8 wherein the skeletal member for replacement includes a lunate and the replacement prosthesis is shaped based on a pre-disease state of the skeletal member for replacement, the replacement prosthesis including caps on articulating surfaces to minimize friction against surrounding bones, the cap will held in place by means of inserts that fit into holes on the surface of the prosthesis.

* * * * *